United States Patent [19]
Brinson et al.

[11] Patent Number: 5,606,090
[45] Date of Patent: Feb. 25, 1997

[54] CONVERSION OF HIGH-BOILING RESIDUE FROM DIRECT PROCESS TO MONOSILANES

[75] Inventors: Jonathan A. Brinson, LaGrange; Steven K. Freeburne, Edgewood; Robert F. Jarvis, Jr., Union, all of Ky.

[73] Assignee: Dow Corning Corporation, Midland, Mich.

[21] Appl. No.: 663,338

[22] Filed: Jun. 13, 1996

[51] Int. Cl.$^6$ .................................................. C07F 7/08
[52] U.S. Cl. ........................................... 556/467; 556/468
[58] Field of Search ..................................... 556/467, 468

[56] References Cited

U.S. PATENT DOCUMENTS

| | | |
|---|---|---|
| 2,380,995 | 8/1945 | Rochow . |
| 2,488,487 | 11/1949 | Barry et al. . |
| 2,598,435 | 5/1952 | Mohler et al. . |
| 2,606,811 | 8/1952 | Wagner . |
| 2,681,355 | 6/1954 | Barry et al. . |
| 3,639,105 | 2/1972 | Atwell et al. . |
| 4,079,071 | 3/1978 | Neale . |
| 4,393,229 | 7/1983 | Ritzer et al. . |
| 5,175,329 | 12/1992 | Bokerman et al. . |
| 5,288,892 | 2/1994 | Pachaly et al. ............... 556/468 X |
| 5,321,147 | 6/1994 | Chadwick et al. ............ 556/468 X |
| 5,430,168 | 7/1995 | Ferguson et al. . |
| 5,502,230 | 3/1996 | Mautner et al. ............... 556/468 |

*Primary Examiner*—Paul F. Shaver
*Attorney, Agent, or Firm*—William F. Boley

[57] ABSTRACT

A process for the production of monosilanes from the high-boiling residue resulting from the reaction of organochlorides with silicon metalloid in a process typically referred to as the "direct process." The present process comprises forming a mixture comprising an organosilane and the high-boiling residue and contacting the mixture in the presence of hydrogen gas with a catalytic amount of a catalyst composition effective in promoting the formation of monosilanes from the high-boiling residue. A preferred catalyst composition comprises aluminum trichloride, at least a portion of which may be formed in situ during conduct of the direct process and isolation of the high-boiling residue.

23 Claims, No Drawings

CONVERSION OF HIGH-BOILING RESIDUE FROM DIRECT PROCESS TO MONOSILANES

BACKGROUND OF INVENTION

The present invention is a process for the production of monosilanes from the high-boiling residue resulting from the reaction of organochlorides with silicon metalloid in a process typically referred to as the "direct process." The present process comprises forming a mixture comprising an organosilane and the high-boiling residue and contacting the mixture in the presence of hydrogen gas with a catalytic amount of a catalyst composition effective in promoting the formation of monosilanes from the high-boiling residue. A preferred catalyst composition for use in the process comprises aluminum trichloride, at least a portion of which may be formed in situ during conduct of the direct process and isolation of the high-boiling residue.

In the preparation of organohalosilanes by the direct process a complex mixture is formed which is typically distilled to separate monosilanes from other components present in the mixture. For example, in the "direct process," in addition to the monosilanes which in the case of the methylchlorosilanes include dimethyldichlorosilane, methyltrichlorosilane, and trimethylchlorosilane there is obtained a residue which boils above the methylchlorosilanes, that is above about 70° C. This residue is hereinafter referred to as "high-boiling residue."

The "direct process" is well described in the patent literature, for example, in Rochow, U.S. Pat. No. 2,380,995, issued Aug. 7, 1945, and Barry et al., U.S. Pat. No. 2,488,487, issued Nov. 15, 1949. The residue remaining after distillation overhead of the monosilanes is a complex mixture comprising higher boiling silicon containing compounds which have, for example, SiSi, SiOSi, and SiCSi linkages in the molecules. The residue may also contain silicon particulates and metals or compounds thereof. Typical high-boiling residues obtained from distillation of product from the direct process are described, for example, in Mohler et al., U.S. Pat. No. 2,598,435, issued May 27, 1952, and Barry et al., U.S. Pat. No. 2,681,355, issued Jun. 15, 1954.

In current commercial operations for performing the direct process, the high-boiling residue can constitute as much as five weight percent of the resultant product. Therefore, it is desirable to convert the high-boiling residue into commercially desirable products to both reduce waste disposal and to improve raw material utilization.

Wagner, U.S. Pat. No. 2,606,811, issued Aug. 12, 1952, teaches a hydrogenation process where a compound containing a halogen and the Si—Si bond is heated to a temperature of at least 300° C. in the presence of hydrogen. The resultant products are monosilanes.

Atwell et al., U.S. Pat. No. 3,639,105, issued Feb. 1, 1972, describe a process where hydrosilanes are produced by contacting a disilane with hydrogen gas under pressure and heating the mixture in the presence of a transition metal catalyst such as palladium on charcoal. Atwell et al. state that the disilane may be part of a mixture from the direct process. Atwell et al. further report that when the disilane was a methylchlorodisilane, the resulting product contained about four to 28 weight percent of methyltrichlorosilane. Generally, organotrihalosilanes such as methyltrichlorosilane have limited commercial usefulness and for this reason limit the usefulness of the process described by Atwell et al.

Neale, U.S. Pat. No. 4,079,071, issued Mar. 14, 1978, describes a process for preparing high yields of hydrosilanes by reacting methylchloropolysilanes with hydrogen gas under pressure at a temperature of from 25° C. to about 350° C. in the presence of a copper catalyst. Neale states that the methylchloropolysilanes can be those typically created as by-products of the direct process. Useful copper catalysts described by Neale include copper metal, copper salts, and complexes of copper salts with organic ligands. Neale reports that in some cases up to 29 weight percent of methyltrichlorosilane was formed.

Ritzer et al., U.S. Pat. No. 4,393,229, issued Jul. 12, 1983, describe a process for converting alkyl-rich disilanes in a residue obtained from the manufacture of alkylhalosilanes to halogen-rich polysilanes. The process comprises treating an alkyl-rich disilane-containing residue with an alkyltrihalosilane or silicon tetrahalide in the presence of a catalyst and a catalytic amount of a hydrosilane reaction promoter at an elevated temperature. Ritzer et al. teach aluminum trichloride as a useful catalyst in their process when used with a hydrosilane promoter. Ritzer et al. further teach that the resulting halogen-rich polysilanes can, in a separate step, be cleaved to form monosilanes.

Bokerman et al., U.S. Pat. No. 5,175,329, issued Dec. 29, 1992, describe a process for the production of organosilanes from the high-boiling residue resulting from the direct process that results in a net consumption of organotrichlorosilane. In the described process the high-boiling residue is contacted with an organotrichlorosilane and hydrogen gas in the presence of both a hydrogenation catalyst and a redistribution catalyst.

Ferguson et al., U.S. Pat. No. 5,430,168, issued Jul. 4, 1995, describe a process for production of monosilanes from the high-boiling residue resulting from the direct process. The process comprises forming a mixture comprising an organotrihalosilane and the high-boiling residue in the presence of hydrogen gas and a catalytic amount of aluminum trichloride.

An object of the present invention is to provide a simple process where the high-boiling residue from a direct process for producing organohalosilanes can be converted into commercially useful monosilanes. The present inventors have discovered that this objective can be met by Contacting the high-boiling residue with an organosilane, hydrogen gas, and a catalytic amount of a catalyst composition effective in promoting the formation of monosilanes from the high-boiling residue. The present process is run as a one-step process with the high-boiling residue, organosilane, and hydrogen gas being fed to a reactor as co-feeds forming a mixture which contacts the catalyst composition to effect formation of monosilanes. The process results in unique product distributions which depend upon the organosilane feed. Therefore monosilane product resulting from the use of a specific organosilane may be used as a co-feed in a subsequent conduct of the process, thereby providing a means of controlling the types of monosilanes produced to match commercial demand.

SUMMARY OF INVENTION

The present invention is a process for the production of monosilanes from the high-boiling residue resulting from the reaction of organochlorides with silicon metalloid in a process typically referred to as the "direct process." The present process comprises forming a mixture comprising an organosilane and the high-boiling residue and contacting the mixture in the presence of hydrogen gas with a catalytic amount of a catalyst composition effective in promoting the formation of monosilanes from the high-boiling residue. A preferred catalyst composition comprises aluminum trichloride, at least a portion of which may be formed in situ during conduct of the direct process and isolation of the high-boiling residue.

DESCRIPTION OF INVENTION

The present invention is a process for converting a high-boiling residue resulting from the reaction of an organochloride with silicon metalloid to monosilanes. The process comprises:

(A) forming a mixture comprising a high-boiling residue resulting from the reaction of an organochloride with silicon metalloid and an organosilane described by formula $$R_mH_nSiCl_{4-m-n}, \quad (1)$$

where each R is independently selected from a group consisting of alkyls comprising one to six carbon atoms, aryls, alkoxys comprising one to six carbon atoms, trimethylsilyl, and trifluoropropyl, m=1 to 4, n=0 to 2, and m+n=2 to 4; and (B) contacting the mixture with hydrogen gas in the presence of a catalytic amount of a catalyst composition effective in promoting the formation of monosilanes from the high-boiling residue at a temperature within a range of about 150° C. to 500° C. and a total reactor pressure within a range of about 100 psig to 5,000 psig.

The present process can further comprise:

(C) recovering monosilanes described by formula $$R_yH_zSiCl_{4-y-z}, \quad (2)$$

where R is as described above, y=0 to 4, z=0 to 3 and y+z=0 to 4.

The present process may be run in any standard pressurizable reactor suitable for contact with chlorosilanes. The process may be run as a batch process or as a continuous process. The process may be run, for example, in a stirred-bed reactor, continuous stirred-tank reactor, a bubble-column reactor, a trickle-bed reactor, or a plug-flow reactor.

The present process is useful for converting a high-boiling residue resulting from the reaction of an organochloride with silicon metalloid to useful monosilanes. In a typical process for reacting an organochloride with silicon metalloid, the process is conducted at a temperature of about 300° C. to 350° C. in the presence of suitable catalysts and gaseous product and feed along with fine particulates are continuously removed from the process. The removed materials are subsequently distilled to recover organochlorosilanes, leaving a "high-boiling residue."

A preferred high-boiling residue for use in the present process is one with a boiling point above about 70° C. resulting from the distillation of methylchlorosilanes from the reaction product of methyl chloride with silicon metalloid. A typical composition for such a high-boiling residue comprises: 50–60 wt % of disilanes of formula $Si_2Q_6$, where each Q is independently selected from a group consisting of methyl and chlorine and the disilane contains two to four methyl substituents per molecule; 15 to 25 weight percent silmethylenes described by formula $Q_3SiCH_2SiQ_3$, where Q is as previously described and the silmethylene contains two to four methyl substituents per molecule; silalkylenes described by formula $Q_3Si(SiQ_2)_a(CH_2)_b(SiQ_2)_cSiQ_3$, where Q is as previously described, the silalkylene contains two to four methyl substituents per molecule, a=0 to 4, b=1 to 3, c=0 to 4, and a+b+c+≧2; 5 to 15 weight percent other high-boiling silicon-containing compounds; catalysts carry over from the direct process such as copper and compounds of copper; particulates containing silicon; and low levels of metals such as aluminum, calcium, and iron and compounds thereof.

As previously discussed, it is known that the high-boiling residue can be treated with a hydrogenation catalyst and hydrogen gas to produce monosilanes. However, a consequence of this hydrogenation process is the production of organotrihalosilanes which have limited commercial utility and therefore are an undesirable product. The present process results in unique product distributions which depend upon the organosilane feed. Therefore monosilane product resulting from the use of a specific organosilane may be used as a co-feed in a subsequent conduct of the process, thereby providing a means of controlling the types of monosilanes produced to match commercial needs. For example, when the organosilane feed is dimethyldichlorosilane a major product of the process is methyldichlorosilane and a smaller amount of dimethylchlorosilane. The methyldichlorosilane can then be used as a feed in a subsequent conduct of the process resulting in dimethyldichlorosilane being a major product. In such a manner the amount of methyldichlorosilane, dimethylchlorosilane, and dimethyldichlorosilane produced by conduct of the process can be controlled to match commercial demand.

In the present process a mixture of the high-boiling residue as described above is formed with an organosilane as described by formula (1). The mixture can be formed external to the reactor and added to the reactor or may be formed by adding the individual components to the reactor. The organosilane contains one to four substituents R, where each R is independently selected from a group consisting of alkyls comprising one to six carbon atoms, aryls, alkoxys comprising one to six carbon atoms, trimethylsilyl, and trifluoropropyl. Substituent R can be, for example, methyl, ethyl, propyl, isopropyl, tert-butyl, methoxy, ethoxy, phenyl, tolyl, naphthyl, trimethylsilyl, and trifluoropropyl. Preferred is when R is methyl.

The organosilane can be, for example, dimethyldichlorosilane, ethylmethyldichlorosilane, methylphenyldichlorosilane, methyl(3,3,3-trifluoropropyl)dichlorosilane, methyldichlorosilane, ethyldichlorosilane, phenyldichlorosilane, trimethylchlorosilane, ethyldimethylchlorosilane, tetramethylsilane, and trimethoxychlorosilane. Preferred is when the organosilane is selected from a group consisting of dimethyldichlorosilane, methyldichlorosilane, trimethylchlorosilane, and tetramethylsilane.

The weight percent of organosilane in the mixture with the high-boiling residue is not critical to the present process. Generally, a mixture where the organosilane is about 0.1 to 95 weight percent of the mixture is considered useful. Preferred is where the organosilane is about 30 to 80 weight percent of the mixture.

The mixture is contacted with hydrogen gas at a reactor pressure within a range of about 100 psig to 5,000 psig. Preferred is a reactor pressure within a range of about 300 psig to 1500 psig. More preferred is a reactor pressure within a range of about 600 psig to 1100 psig. The above cited reactor pressures refer to the total pressure within the reactor.

The amount of hydrogen gas added to the process is not critical and can be any amount sufficient to effect an acceptable level of hydrogenation. Generally about 0.05 to 10 weight percent hydrogen gas is considered useful in the process, based upon the total weight of the mixture, hydrogen gas, and catalyst composition present in the process.

Preferred is when the hydrogen gas is added to the process within a range of about 1 to 5 weight percent, on the same basis.

The mixture comprising the high-boiling residue and organosilane, in the presence of hydrogen gas, is contacted with a catalytic amount of a catalyst composition effective in promoting formation of monosilane from the high-boiling residue. The catalyst composition required in the present process promotes the formation of monosilanes from the high-boiling residue. The present inventors believe that the process requires a catalytic composition which promotes redistribution of alkyl and chlorine groups between silicon atoms, hydrogenation, and scission of silicon-silicon bonds and optionally silicon-carbon bonds. Therefore, the catalyst composition can comprise one or more chemical entities providing the described activities to the catalytic composition.

Generally, any Lewis Acid or its equivalent may be used to provide redistribution activity to the catalyst composition. Examples of chemical entities useful to effect redistribution in the present process include those described in Ritzer et al., U.S. Pat. No. 4,393,229, issued Jul. 12, 1983, and in Bokerman et al., U.S. Pat. No. 5,175,329, issued Dec. 29, 1992, which are hereby incorporated by reference for their teaching of such redistribution catalyst. Examples of such chemical entities useful to effect redistribution in the present process include aluminum trichloride, antimony pentachloride, zirconium tetrachloride, potassium aluminum tetrachloride, quaternary phosphonium halides, quaternary ammonium halides, ammonium halides, cuprous chloride, boric acid, and boron halides.

Examples of chemical entities useful in the catalyst composition to effect hydrogenation include those hydrogenation catalysts described in Bokerman et al., U.S. Pat. No. 5,175,329, issued Dec. 29, 1992, which is hereby incorporated by reference for such teachings. The chemical entity providing hydrogenation activity to the catalyst composition can be, for example, aluminum trichloride, antimony pentachloride, nickel, supported nickel, organometallic nickel compounds, complexed nickel salts, inorganic nickel compounds, palladium, supported palladium, organometallic palladium compounds, complexed palladium salts, inorganic palladium compounds, platinum, supported platinum, organometallic platinum compounds, complexed platinum salts, and inorganic platinum compounds.

Generally those chemical entities which promote redistribution of alkyl groups and chlorine atoms between silicon atoms and those chemical entities which promote hydrogenation in the present process also promote scission of silicon—silicon bonds and optionally silicon-carbon bonds. Therefore, it is generally not necessary to add additional chemical entities to the catalyst composition to promote the scission of the silicon—silicon bonds and optionally silicon-carbon bonds. If such chemical entities are needed a chemical entity such as aluminum trichloride or antimony pentachloride may be added to the catalyst composition.

In the present process it is preferred that the catalyst composition comprise a single chemical entity which promotes redistribution, hydrogenation, and bond scission under process conditions. Such single chemical entities include aluminum trichloride and antimony pentachloride.

The present process requires the presence of a "catalytic amount" of a catalyst composition as described above. By the term "catalytic amount" it is meant an amount of catalyst composition sufficient to facilitate the conversion of silicon containing compounds in the high-boiling residue to monosilanes. A preferred catalytic amount of catalyst composition is that sufficient to facilitate the conversion of polysilanes, for example methylchlorosilanes, silmethylenes, and silalkylenes in the high-boiling residue to monosilanes. The amount of catalyst composition required will depend upon the chemical entities comprising the catalyst composition, and such amounts can be easily determined by those skilled in the art.

When aluminum trichloride or antimony pentachloride comprise the catalyst composition, about 0.01 to 20 weight percent of catalyst composition based on the combined weight of the catalyst composition and the high-boiling residue is considered useful in the present process. When aluminum trichloride or antimony pentachloride comprises the catalyst composition a preferred weight of catalyst composition in the process is within a range of about 0.5 to 5 weight percent, on the same basis.

A preferred catalyst composition for use in the present process is aluminum trichloride. The aluminum trichloride may be added to the process as the compound or may be formed in situ by the addition of materials that form aluminum trichloride. All or a portion of the catalytic amount of aluminum trichloride may be formed in situ during conduct of the direct process and isolation of the monosilane fraction to form the high-boiling residue. The source of the aluminum and chlorine necessary to form the aluminum trichloride can be the raw materials used in the direct process, particularly the silicon metalloid and organochloride feed. The catalytic amount of aluminum trichloride can be a combination of added aluminum trichloride and in situ formed aluminum trichloride remaining in the high-boiling residue as isolated from the direct process.

The present process can be conducted at a temperature within a range of about 150° C. to 500° C. Preferred is a temperature within a range of about 275° C. to 425° C. Most preferred is a temperature within a range of about 300° C. to 350° C.

Monosilanes as described by formula (2) are recovered from the present process. The monosilanes can be separated by standard methods for separating liquid mixtures, for example, distillation. The monosilanes can contain zero to four substituents R, where R is as previously described. The monosilane can contain zero to three hydrogens substituted on each silicon atom. The monosilanes can contain zero to four chlorine atoms substituted on each silicon atom. A preferred monosilane is selected from a group consisting of dimethyldichlorosilane, methyldichlorosilane, and dimethylchlorosilane.

The following examples are provided to illustrate the present invention. These examples are not intended to limit the claims herein. In the examples, Me represents the methyl radical.

EXAMPLES

The ability of aluminum trichloride to catalyze the conversion of a high-boiling residue was evaluated in a stirred-batch reactor using various methylchlorosilanes as co-feed.

The reactor was a 650 ml, pneumatically stirred, Parr Bomb reactor. About 0.15 mole (Mol) of a high boiling residue from a direct process for the preparation of methylchlorosilanes by the reaction of methyl chloride with silicon metalloid was added to the reactor. The high-boiling residue was the fraction remaining in the bottom of a still after distilling off the monosilane fraction at about 70° C. The high-boiling residue was filtered to reduce particulates. The major components of the high-boiling residue used in each example run in presented in Table 1 on a weight percent basis.

TABLE 1

Major Components of High-Boiling Residue

| | Run Designation | | | | |
|---|---|---|---|---|---|
| Component | C | D | E | F | G |
| | (Weight Percent) | | | | |
| $Cl_2MeSiSiMe_3$ | 0.4 | 0.7 | 1.2 | 0.5 | 0.5 |
| $ClMe_2SiSiMe_2Cl$ | 6.2 | 2.2 | 1.1 | 2.2 | 2.4 |
| $Cl_2MeSiSiMe_2Cl$ | 32.2 | 15.3 | 16.8 | 5.6 | 9.3 |
| $Cl_2MeSiSiMeCl_2$ | 53.5 | 15.3 | 16.9 | 15.4 | 15.2 |
| $ClMe_2SiCH_2SiMe_2Cl$ | 0.8 | 2.2 | 1.1 | 0.5 | 0.5 |
| $Cl_2MeSiCH_2SiMe_2Cl$ | 3.2 | 3.1 | 3.1 | 1.5 | 1.8 |
| $Cl_2MeSiCH_2SiMeCl_2$ | 3.7 | 3.1 | 2.7 | 2.2 | 2.6 |

For each run 3 to 4 weight percent of aluminum chloride, based on the high-boiling residue weight, was present in the high-boiling residue. About 0.9 to 1 mole of hydrogen gas at a pressure within a range of 1000 to 1400 psig was added to the reactor for each run and the reactor was heated to about 325° C. and stirred for about 2.8 hours. The type and amount of organosilane fed to the reactor is as follows: Run C, none; Run D, 55 weight percent of $MeSiCl_3$; Run E, 54.2 weight percent of $Me_2SiCl_2$; Run F, 70.3 weight percent of $MeH_2SiCl_2$; and Run G, 65 weight percent of $Me_3SiCl$.

At the end of each run a sample from the reactor was analyzed by gas chromatography (GC) using a thermal conductivity detector (TCD). The results of this analysis are reported in Table 2. The product distribution for each run is present in Table 2 as a net value calculated as the weight percent each species of monosilane represents of the total monosilanes present in the product. In Table 2, the weight percent of the high-boiling residue converted to monosilane product is reported in the row labelled "HBR Conversion".

TABLE 2

Product Conversion and Distribution

| | Run Designation | | | | |
|---|---|---|---|---|---|
| Monosilane | C | D | E | F | G |
| | (Weight Percent) | | | | |
| $MeSiCl_3$ | 22.3 | 0.0 | 25.2 | 39.2 | 3.8 |
| $Me_2SiCl_2$ | 27.2 | 28.3 | 1.0 | 45.1 | 64.3 |
| $Me_3SiCl$ | 1.2 | 0.7 | 9.6 | 1.6 | 0.0 |
| $McHSiCl_2$ | 34.7 | 48.6 | 43.9 | 0.0 | 9.9 |
| $Me_2HSiCl$ | 9.6 | 3.1 | 16.1 | 6.3 | 15.6 |
| $MeH_2SiCl$ | 4.3 | 5.6 | 4.1 | 7.6 | 2.4 |
| $HSiCl_3$ | 0.8 | 0.0 | 0.7 | 0.3 | 0.0 |
| HBR Conversion | 66.2 | 81.2 | 94.4 | 89.5 | 89.5 |

We claim:
1. A process for converting a high-boiling residue resulting from the reaction of an organochloride with silicon metalloid to monosilanes, the process comprising:
 (A) forming a mixture comprising a high-boiling residue resulting from the reaction of an organochloride with silicon metalloid and an organosilane described by formula

$$R_mH_nSiCl_{4-m-n},$$

where each R is independently selected from a group consisting of alkyls comprising one to six carbon atoms, aryls, alkoxys comprising one to six carbon atoms, trimethylsilyl, and trifluoropropyl, m=1 to 4, n=0 to 2, and m+n=2 to 4; and
 (B) contacting the mixture with hydrogen gas in the presence of a catalytic amount of a catalyst composition effective in promoting the formation of monosilanes from the high-boiling residue at temperature within a range of about 150° C. to 500° C. and a reactor pressure within a range of about 100 psig to 5,000 psig.

2. A process according to claim 1, where the high-boiling residue has a boiling point above about 70° C. and results from the distillation of methylchlorosilanes from the reaction product of methyl chloride with silicon metalloid.

3. A process according the claim 2, where the organosilane is selected from a group consisting of dimethyldichlorosilane, methyldichlorosilane, trimethylchlorosilane, and tetramethylsilane.

4. A process according to claim 2, where the organosilane is dimethyldichlorosilane.

5. A process according to claim 2, where the organosilane is methyldichlorosilane.

6. A process according to claim 2, where the organosilane is trimethylchlorosilane.

7. A process according to claim 1, where the organosilane comprises about 0.1 to 95 weight percent of the mixture.

8. A process according to claim 1, where the organosilane comprises about 30 to 50 weight percent of the mixture.

9. A process according to claim 1, where the reactor pressure is within a range of about 300 psig to 1500 psig.

10. A process according to claim 1, where the reactor pressure is within a range of about 600 psig to 1100 psig.

11. A process according to claim 1 comprising about 0.05 to 10 weight percent hydrogen gas based on,the total weight of the mixture, hydrogen gas, and catalyst composition added to the process.

12. A process according to claim 1, comprising about 1 to 5 weight percent hydrogen gas based on the total weight of the mixture, hydrogen gas, and catalyst composition added to the process.

13. A process according to claim 1, where the catalyst composition is selected from a group consisting of aluminum trichloride and antimony pentachloride.

14. A process according to claim 1, where the catalyst composition consist essentially of aluminum trichloride.

15. A process according to claim 1, where the catalyst composition consist essentially of antimony pentachloride.

16. A process according to claim 13, where the catalyst composition comprises about 0.01 to 20 weight percent of the combined weight of the catalyst composition and the high-boiling residue.

17. A process according to claim 13, where the catalyst composition comprises about 0.5 to 5 weight percent of the combined weight of the catalyst composition and the high-boiling residue.

18. A process according to claim 1, where the temperature is within a range of about 275° C. to 500° C.

19. A process according to claim 1, where the temperature is within a range of about 300° C. to 350° C.

20. A process according to claim 1 further comprising recovering monosilanes described by formula $$R_yH_zSiCl_{4-y-z},$$

where R is as previously described, y=0 to 4, z=0 to 3, and y+z=0 to 4.

21. A process according to claim 20, where the monosilane is selected from a group consisting of dimethyldichlorosilane, methyldichlorosilane, and dimethylchlorosilane.

22. A process for converting a high-boiling residue resulting from the reaction of methyl chloride with silicon metalloid to monosilanes, the process comprising:

(A) forming a mixture comprising a high-boiling residue having a boiling point greater than about 70° C. resulting from the distillation of the reaction product of methyl chloride with silicon metalloid and an organosilane selected from a group consisting of dimethyldichlorosilane, methyldichlorosilane, trimethylchlorosilane, and tetramethylsilane; and (B) contacting the mixture with 1 to 5 weight percent hydrogen, based on the weight of the mixture, hydrogen gas, and aluminum trichloride added to the process; in the presence of 0.1 to 1 weight percent aluminum trichloride, based upon the combined weight of the mixture and the aluminum trichloride; at a temperature within a range of about 300° C. to 350° C.; and a reactor pressure within a range of about 600 psig to 1100 psig.

23. A process according to claim 22, where at least a portion of the catalytic amount of the aluminum trichloride is formed in situ.

* * * * *

UNITED STATES PATENT AND TRADEMARK OFFICE
CERTIFICATE OF CORRECTION

PATENT NO. : 5,606,090

DATED : February 25, 1997

INVENTOR(S) : Jonathan Ashley Brinson, Steven Kerry Freeburne and Robert Frank Jarvis, Jr.

It is certified that error appears in the above-identified patent and that said Letters Patent are hereby corrected as shown below:

Column 1, line 6, should read "This invention was made with United States Government support under DOE Contract DE-FC04-94AL99566 awarded by the Department of Energy. The United States Government has certain rights in the invention".

Signed and Sealed this

Second Day of December, 1997

Attest:

BRUCE LEHMAN

Attesting Officer

Commissioner of Patents and Trademarks